US005982485A

United States Patent [19]
Schrof et al.

[11] Patent Number: 5,982,485
[45] Date of Patent: Nov. 9, 1999

[54] DETERMINATION OF INTERFACE ADSORPTION

[75] Inventors: Wolfgang Schrof, Neuleiningen; Frank Runge, Maxdorf; Jürgen Klingler, Mutterstadt, all of Germany

[73] Assignee: BASF Aktiengesellschaft, Ludwigshafen, Germany

[21] Appl. No.: 09/092,969

[22] Filed: Jun. 8, 1998

[30] Foreign Application Priority Data

Jun. 9, 1997 [DE] Germany .............. 197 24 238

[51] Int. Cl.⁶ .................................................. G01D 3/44
[52] U.S. Cl. .................... 356/301; 356/337; 356/432; 356/445
[58] Field of Search ................... 356/301, 337, 356/432, 445

[56] References Cited

U.S. PATENT DOCUMENTS 5,744,709  4/1998  Saripalli et al. .

OTHER PUBLICATIONS

Bestimmung der Grenzflachenbesetzungskinetik, Anbarci et al., 1987, 111.

*Primary Examiner*—Frank G. Font
*Assistant Examiner*—Reginald A. Ratliff
*Attorney, Agent, or Firm*—Keil & Weinkauf

[57] ABSTRACT

A method and an apparatus for determining the coverage of the interface between a liquid first phase and a liquid or gaseous second phase by at least one molecular species, at least the following procedural steps being carried out successively: the generation of a stream of droplets which contain at least the liquid first phase, in such a way that the droplets move along a droplet trajectory, and the non-contact determination of a measure of the coverage of the interface by the at least one molecular species at at least two different points along the droplet trajectory.

12 Claims, 1 Drawing Sheet

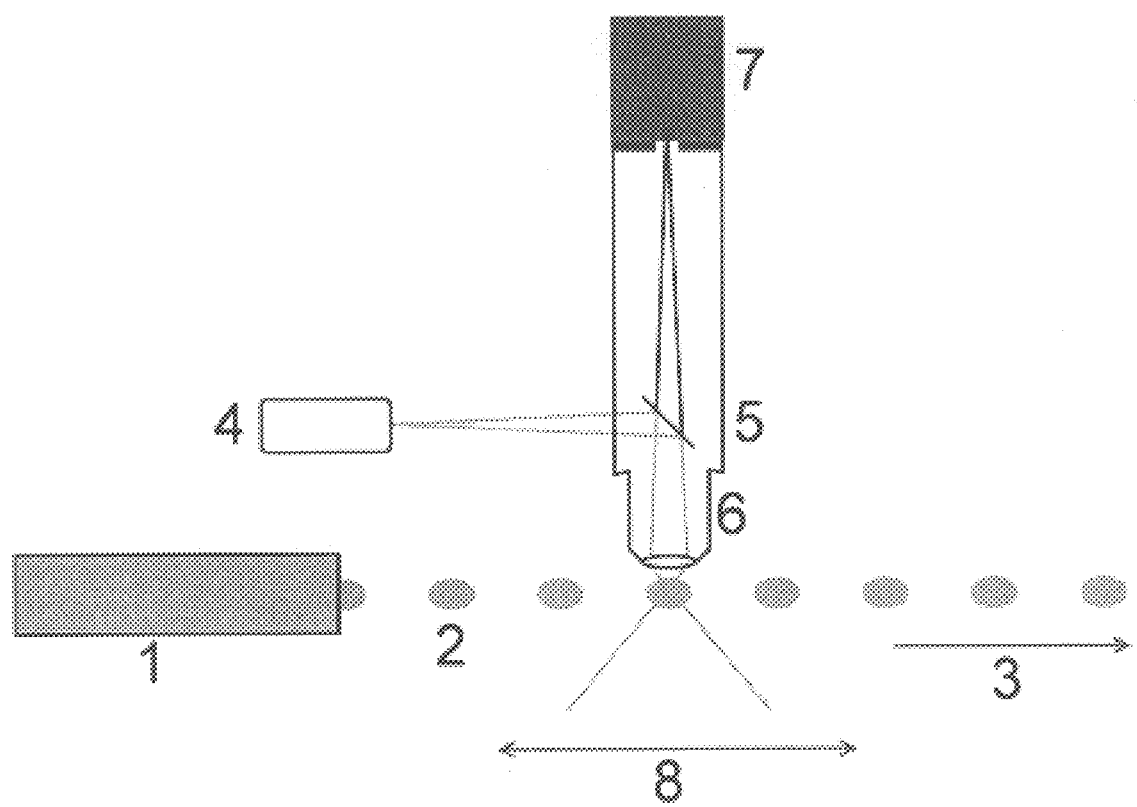

DETERMINATION OF INTERFACE ADSORPTION

The present invention relates to a method and an apparatus for determining interface adsorption, in particular the kinetics of interface adsorption of substances.

In the course of developing surfactants, emulsifiers, protective colloids and many other surface-active substances, it is necessary to determine various parameters of interface activity. One of these parameters is interface adsorption. This variable indicates what percentage of the interface of two test substances is covered by a further test substance. Of interest in this context is not only the eventual equilibrium state established in a static system, but also, and indeed primarily, the dynamic development up to this end state.

Known methods for determining interface adsorption, however, can only be used to a limited extent to observe dynamic processes. This is because, using these methods, the development over time of a system must always be observed directly, ie. in real time in terms of the dynamics. For example, the bursting-membrane method as described by A. Anbarci and A. Armbruster in "Bestimmung der Grenzflächenbesetzungskinetik [Determination of interface coverage kinetics]", Tenside Surfactants Detergents 24 (1987) 2, 111, is regarded as reliable only when it is used to observe changes which proceed in a time range of a few hundredths of a second or more slowly. Indeed, the resolution of the classic Wilhelmi plate or Wilhelmi balance is only in the order of magnitude of a second. Many interesting dynamic phenomena, however, occur in the millisecond range or even in the submillisecond range. Conventional measuring methods cannot be used for determining them with sufficient reliability.

It is therefore an object of the present invention to provide a method for determining interface adsorption, which method can be used to observe dynamic interface processes even when they proceed very rapidly. Moreover, this measuring method should be largely insensitive to contamination and external disturbances.

We have found that this object is achieved by the method according to the invention for determining the coverage of the interface between a liquid first phase and a liquid or gaseous second phase by at least one molecular species. According to the invention, this involves at least the following procedural steps being carried out successively. First a stream of droplets which contain at least the liquid first phase is generated in a droplet generator, in such a way that the droplets move along a specific droplet trajectory, where the medium surrounding the droplets may be a gas, a vacuum or a liquid. The phase interface to be studied can be formed either inside the droplets, if these contain both phases, or at the surface of the droplets. Then whatever suitable parameter required which is indicative of the coverage of the interface by the at least one molecular species is determined, without contact being made, at at least two different points along the droplet trajectory. In other words, the same or a similar droplet is observed at at least two different distances from the droplet generator, the distance of a droplet from the droplet generator corresponding to the age of said droplet. But the age, in turn, correlates directly with the state of development of the droplet. Thus it is possible to study the dynamics of an interface process without the temporal resolution of the measuring method having to meet any special requirements. Instead of a temporal resolution which is not readily achievable, the method according to the invention therefore employs a readily implementable spatial resolution of the development process.

Depending on the level of detail, ie. temporal resolution, to which the development process at the interface in question is to be monitored at the same time, the same or similar droplets are studied at more or fewer measuring stations spaced further apart or closer together along their flight trajectory, the droplet trajectory. This can be achieved by the detector for the particular parameter indicative of the interface coverage being shifted along the droplet trajectory. Often, however, it will be more practical to arrange a plurality of detectors of the same type along the droplet trajectory and to use these for the simultaneous observation of a plurality of droplets, each in a different stage of development. The data obtained can then be assigned to each particular droplet, so that it is possible to reconstruct its evolution. In particular it is possible to use the method according to the invention to observe and research the stabilization or, alternatively, coalescence of systems such as emulsions and suspensions.

With the method according to the invention, the droplet generator used may in principle be any apparatus which is suitable for generating a regular succession of liquid droplets of defined size. Preference is given to the use of a droplet generator with which, by contraction and relaxation of a contraction element, one or more droplets are, at regular intervals, separated from a liquid column and expelled. This contraction element is preferably actuated piezomechanically, ie. using a piezo crystal. Alternatively, the droplet generator used may be an apparatus which involves a stream of liquid being forced through a nozzle, around which an enveloping stream of a second liquid is flowing in a suitable manner.

In a preferred method, the droplet stream is formed by the merging of at least two originally generated droplet streams, in each case droplets from the originally formed droplet streams mixing with one another. As a rule, two original droplet streams will be used, of which one contains the first phase and the other contains the second phase. This ensures a precisely defined zero time for the measurement, ie. the instant of mixing of the original streams. Moreover, as a result of the rapid merging of the streams, it is possible to achieve very good mixing of the phases, which is desirable for a number of measurements.

The generated droplets are expelled from the droplet generator at regular intervals and then, during the measuring phase, move on a predefined droplet trajectory until they are collected in a collection vessel and discharged. During the measuring phase, the droplet trajectory, ie. the flight trajectory of the generated droplets, preferably runs in a gas atmosphere, preferably an inert gas atmosphere such as, for example, a nitrogen or argon atmosphere, so that interface effects occurring at the droplet surface can be observed with as little interference as possible. Alternatively, however, the droplet trajectory can pass through a gas atmosphere or a liquid environment. Correspondingly, it is possible to study interface effects at interfaces between gases and liquids and between two liquids. In this context, the molecular species whose coverage of the interface is to be studied may form part of the gas atmosphere or of the liquid environment. Alternatively, the molecular species may already be present in the generated and expelled droplets. To this end, the molecular species is admixed to the first phase in the droplet generator. This will be preferred as a rule, since, in this case, expelling the just-mixed droplets from the droplet generator into the droplet trajectory defines a constant temporal reference from which the interface coverage to be observed will occur.

The second phase which, together with the first phase, forms the interface under consideration may, according to the invention, be present in the droplets, so that the interface forms within the droplets; alternatively, it may surround the droplets along the droplet trajectory, so that the interface under consideration is the droplet surface. Like the first phase, said second phase may comprise a mixture of a plurality of substances, subject only to the precondition that an interface be able to form between the first and the second phases.

Since relatively small-volume droplets are observed, the risk of the measuring volume becoming contaminated is markedly reduced. As long as the droplet generator is not contaminated, any contamination of individual droplets is insignificant, given the amount of droplets measured regularly. Should contamination occur, all that is necessary is to eliminate the individual measured data in question, while the remaining measured data can continue to be used without any restrictions. The novel method is therefore considerably less sensitive to external contamination than the methods known hitherto.

Nor does the use of the invention require the system to be in thermodynamic equilibrium or ultimately to achieve more or less complete coverage of the interface. The present invention can be used, ultimately, to study all surface-active systems which allow the detection of a signal which correlates with interface coverage.

The parameter indicative of the coverage of the interface with molecules can be any output signal whose intensity or nature depends on the quantity of the coverage. If quantitative statements are to be made, this dependence of the output signal on the coverage must be known or determinable, ie. calibration must be possible.

Examples of suitable output signals are the reflection, scattering or transmission of light, in particular laser light, injected into the droplet trajectory. Since these measured quantities depend markedly on interface coverage, especially if the interface is identical to the droplet surface, their change along the droplet trajectory permits inferences regarding interface-adsorption dynamics. Other suitable measured quantities include Raman scattered light signals and fluorescent light signals which make it possible to distinguish between various substances and whose wavelength and intensity are primarily determined by the molecules situated at the interface, especially the droplet surface. In this context, fluorescence signals may originate from the observed molecular species or a marker substance. Alternatively, however, radioactively tagged substances or molecules can be used.

A preferred method for observing the effects at the interface is confocal microscopy. Preferably this involves focusing on the interface within or on the droplets moving along the droplet trajectory. This does, however, require a constant flight trajectory of the droplets, which in turn requires a droplet generator whose droplet size and droplet expelling velocity are constant. If these preconditions are met, a confocal microscope can be used for the direct observation of interface developments, for example of a particular molecular species, at the droplet interface. Conversely, if other droplet regions or droplet layers are focused on, it is possible to determine the depletion of particular molecules.

Preferably, within the context of the present invention, use is made of morphology dependent resonances (MDR) spectroscopy. This involves utilizing field resonance, close to the interface, in oscillation modes of the light in each particular droplet, in order to obtain a fluorescence signal or a Raman scattered light signal which depends almost exclusively on the interface coverage.

Further measuring methods suitable in principle within the context of the invention include those which involve the marking of a particle species, so that it is possible to detect the appearance of this species on the interface. Relevant examples include particles labelled with fluorescent or radioactive markers.

According to the invention, an apparatus is also provided for determining the coverage of an interface between a liquid first phase and a liquid or gaseous second phase by at least one molecular species, the apparatus comprising at least the following components: a droplet generator which is designed and arranged in such a way that it is able to generate droplets which contain at least the liquid first phase and which move along a droplet trajectory, and a detector which is designed and arranged in such a way that it is able to determine, without contact being made, a measure of the coverage of the interface in the droplet trajectory by the at least one molecular species. Such an apparatus can be used to implement the above-described method.

Preference is given to an apparatus comprising at least two droplet generators which are designed and arranged in such a way that they each generate an original droplet stream and these original droplet streams are merged to form the droplet stream being studied.

The present invention is described below with reference to FIG. 1. This shows an apparatus according to the invention which can be used to implement the method according to the invention.

The apparatus according to FIG. 1 comprises a droplet generator I which generates and expels uniform droplets 2 at regular intervals. The droplets 2 then move on a droplet trajectory or flight trajectory, here indicated by arrow 3. A laser 4 is arranged in such a way that it is able to inject laser light into the droplet trajectory via the semisilvered mirror 5 and the lens 6. The light reflected by the droplets 2, in particular by the molecules at the droplet surface, is passed to a detector 7 via the lens 6 and the semisilvered mirror 5. The detector 7 can be shifted along the droplet trajectory in the direction of the double arrow 8, so that droplets 2 of varying age, ie. with surface coverages in different stages of evolution, can be observed. The detected signals can then be analyzed in an analyzer unit (not shown).

The measuring apparatus shown in FIG. 1 can be modified in the ways previously mentioned above. Thus it is possible, in particular, to replace the movable detector 7 by a series of fixed detectors along the flight trajectory 3. It is also possible to provide a vacuum cuvette which contains the droplet trajectory 3 during the measurement of the interface effects. Finally, it is also possible to use a number of different parameters indicative of interface coverage, as has already been explained above.

The novel apparatus and the novel method thus permit rapid non-contact and largely contamination-proof determination of the interface adsorption of substances.

We claim:

1. A method for determining the coverage of the interface between a liquid first phase and a liquid or gaseous second phase by at least one molecular species, wherein the following procedural steps are carried out successively:
    a) generation of a stream of droplets which contain at least the liquid first phase, in such a way that the droplets move along a droplet trajectory, and
    b) non-contact determination of a measure of the coverage of the interface by the at least one molecular species at at least two different points along the droplet trajectory.

2. A method as claimed in claim 1, wherein the droplets contain the first and the second phases.

3. A method as claimed in claim 2, wherein the droplets are guided along the droplet trajectory in an inert gas atmosphere.

4. A method as claimed in claim 1, wherein the generation of a stream of droplets in procedural step a) is effected by means of an apparatus for the piezomechanical contraction of a column of liquid.

5. A method as claimed in claim 1, wherein in procedural step b) the determination of the measure of the coverage is effected by a measurement of the reflection, scattering or transmission of light, preferably laser light, injected into the droplet trajectory.

6. A method as claimed in claim 1, wherein in procedural step b) the determination of the measure of the coverage is effected by a measurement of the Raman scattering of light injected into the droplet trajectory.

7. A method as claimed in claim 1, wherein in procedural step b) the determination of the measure of the coverage is effected by a measurement of fluorescent light or radioactive radiation which is emitted by the droplets.

8. A method as claimed in claim 1, wherein in procedural step b) the determination of the measure of the coverage is effected by a measurement by means of MDR spectroscopy on the droplets.

9. A method as claimed in claim 1, wherein in procedural step b) the determination of the measure of the coverage is effected by a measurement by means of confocal microscopy involving focusing on the surface of the droplets.

10. A method as claimed in claim 1, wherein in procedural step a) the stream of droplets is generated by at least two streams of droplets being merged with one another.

11. An apparatus for determining the coverage of an interface between a liquid first phase and a liquid or gaseous second phase by at least one molecular species, wherein the apparatus comprises at least the following components:

a droplet generator which is designed and arranged in such a way that it is able to generate droplets which contain at least the liquid first phase and which move along a droplet trajectory, and a detector which is designed and arranged in such a way that it is able to determine, without contact being made, a measure of the coverage of the interface by the at least one molecular species in the droplet trajectory.

12. An apparatus as claimed in claim 11, which comprises at least two droplet generators which are designed and arranged in such a way that they each generate a stream of droplets which are merged to form a single stream of droplets.

* * * * *